United States Patent [19]

Wong et al.

[11] Patent Number: 5,130,142
[45] Date of Patent: Jul. 14, 1992

[54] HAIR GROWTH REGULATING COMPOSITION COMPRISING EPITHELIUM CELL SUPERNATANT-DERIVED GROWTH FACTOR

[75] Inventors: Teresa K. Wong; Raphael Warren, both of Cincinnati, Ohio

[73] Assignee: The Practer & Gamble Company, Cincinnati, Ohio

[21] Appl. No.: 606,289

[22] Filed: Oct. 31, 1990

[51] Int. Cl.$^5$ .......................... A61K 31/505
[52] U.S. Cl. ................... 424/574; 514/256; 514/880
[58] Field of Search ............ 514/256, 880; 424/70, 424/574

[56] References Cited

U.S. PATENT DOCUMENTS

| 2,551 | 4/1842 | Clirehugh | 424/70 |
|---|---|---|---|
| 101,722 | 4/1870 | Fletcher | 424/721 |
| 110,058 | 12/1870 | Maxfield | 424/70 |
| 253,594 | 2/1882 | Forbes | 424/70 |
| 260,570 | 7/1882 | Hughes | 424/70 |
| 321,487 | 7/1885 | Damann | 424/70 |
| 421,675 | 2/1890 | Crooks et al. | 424/70 |
| 578,632 | 3/1897 | Fleming | 424/647 |
| 1,732,120 | 10/1929 | Christen | 514/678 |
| 3,466,364 | 9/1969 | Takahashi et al. | 424/70 |
| 4,139,619 | 2/1979 | Chidsey | 424/45 |
| 4,832,946 | 5/1989 | Green | 424/70 |
| 5,037,643 | 8/1991 | Green | 424/70 |
| 5,091,173 | 2/1992 | Buultjens et al. | 424/70 |

FOREIGN PATENT DOCUMENTS

| 0215274 | 5/1987 | European Pat. Off. | 17/00 |
|---|---|---|---|
| 0236014 | 9/1987 | European Pat. Off. | 35/36 |
| 272920 | 6/1988 | European Pat. Off. | |
| 352894 | 1/1990 | European Pat. Off. | |
| 2571615 | 7/1984 | France | |
| 61005006 | 6/1984 | Japan | |
| 89/07425 | 8/1989 | World Int. Prop. O. | 2/00 |
| 90/06100 | 6/1990 | World Int. Prop. O. | |

OTHER PUBLICATIONS

The Merck Index, 11th Edition, 6122, Minoxidil.
Couchman, J. R., (1986) "Rat Hair Follicle Dermal Papillae Have an Extracellular Matrix Containing Basement Membrane Components", Dermal Papilla Extracellular Matrix, vol. 87, pp. 762-767.
Bertolino, A. P., D. M. Checkla, S. Heitner, I. M. Greedberg, D. Yu, (1990) "Differential Expression of Type I Hair Keratins", The Journal of Investigative Dermatology, vol. 94, pp. 297-302.
"Growth Regulation of Skin Cells by Epidermal Cell-Derived Factors: Implications for Wound Healing", Procedures National Academy of Sciences, vol. 85, pp. 1937-1941, M. S. Eisinger, S. Sadan, I. A. Silver and R. B. Flick, (Mar. 1988).
"Dermal-Epidermal Interactions", Clinics in Dermatology, vol. 6, pp. 74-82, R. F. Oliver, C. A. B. Jahoda (1988).
"Direct Effects of Minoxidil on Epidermal Cells in Culture", The Journal of Investigative Dermatology, vol. 82, pp. 90-93, R. L. Cohen, M. E. A. F. Alves, V. C. Weiss, D. P. West & D. A. Chanbers, (1984).
"The Induction of Hair Follicle Formation in the Adult Hooded Rat by Vibrissa Dermal Papillae", Journal of Embryology and Experimental Morphology, vol. 23, pp. 219-236, R. F. Oliver (1970).
Chemical Abstracts (110:141235g) 1989.
Chemical Abstracts (113:22276y) 1990.
Chemical Abstracts (113:197659c) 1990.

*Primary Examiner*—Frederick E. Waddell
*Assistant Examiner*—K. Weddington
*Attorney, Agent, or Firm*—B. J. Corstanje; M. B. Graff, IV; J. J. Yetter

[57] ABSTRACT

The present invention relates to a composition for regulating hair growth comprising a safe and effective amount of a supernatant derived from a culture of epithelial cells which comprises a growth stimulating factor with characteristics of mitogenicity to dermal papilla cells, mitogenicity to 3T3 cells, lack of mitogenicity to epidermal cells, and a molecular weight of greater than about 3,000D; and a pharmaceutically-acceptable carrier.

11 Claims, No Drawings

HAIR GROWTH REGULATING COMPOSITION COMPRISING EPITHELIUM CELL SUPERNATANT-DERIVED GROWTH FACTOR

TECHNICAL FIELD

The present invention relates to novel compositions which regulate hair growth.

BACKGROUND OF THE INVENTION

Society in general continues to attach a stigma to hair loss. The desire for a healthy full head of hair has resulted in a variety of approaches to the "curing" of baldness. Investigation of the hair bulb has been among the multitude of hair growth studies that have been reported in the literature. There are two essential features of the hair follicle. These include the epithelia and a specialized dermal compartment called the dermal papilla. The epithelia give rise to to the epidermal stem cells which in turn give rise to the outer root sheath, giving rise to the matrix cell, which gives rise to the inner root sheath and hair fiber. The size of the dermal papilla is related to the size of the hair follicle, and the size of the follicle is related to the size of the hair produced. For example, terminal hair follicles on the scalp of haired individuals are longer and produce long, thick hair. These follicles contain large dermal papilla. In contrast, vellus follicles commonly observed on a bald scalp are small and produce short, thin hair. These vellus follicles contain a small dermal papilla. Similar observations relating to the relationship between the size of the papilla and the hair follicle, and ultimately hair growth, have been made in animals having fur. The specific factors which regulate the size of the dermal papilla may ultimately regulate hair growth.

European Patent Application No. 0,215,274, Eisinger, assigned to the Memorial Hospital for Cancer and Allied Diseases, published Mar. 25, 1987, discloses the sonification of epidermal cells to extract the intracellular materials. Methods to enhance wound healing, regenerate epidermis, and enhance hair growth via application of the epidermal cell extract are also diclosed.

Eisinger, M., S. Sadan, I. A. Silver and R. B. Flick, (Mar. 1988) "Growth Regulation of Skin Cells by Epidermal Cell-Derived Factors: Implications for Wound Healing", *Procedures of the National Academy of Sciences*, Vol. 85, pp. 1937–1941, discloses an epidermal cell-derived growth factor derived by sonification of the epidermal cells or from a cell free supernatant. The factor has the following characteristics: 1) it is directly mitogenic to epidermal cells; 2) it is not directly mitogenic to 3T3 cells; 3) it directly inhibits fibroblast metabolic activity; and 4) it has an approximate molecular weight of 1000 daltons.

World Patent Application 89/07425, Sackier, Wood, Krishnan and Wigginton, assigned to Genethics Ltd., published Aug. 24, 1989, claims an ointment, lotion, cream or gel containing amnion epithelial cells and extracts from such epithelial cells dispersed in a pharmaceutically acceptable carrier. '07245 further discloses that such a composition may be used to stimulate hair follicle and hair growth.

OBJECTS OF THE PRESENT INVENTION

It is an object of the present invention to provide compositions for regulating hair growth.

It is a further object of the present invention to provide compositions for regulating hair growth which are suitable for topical application.

It is also an object of the present invention to provide compositions for regulating hair growth which are suitable for application via cutaneous injection.

It is also an object of the present invention to provide methods for regulating hair growth which comprise applying to mammalian skin or hair a topical composition.

It is also an object of the present invention to provide methods for regulating hair growth which comprise cutaneous injection of a composition.

SUMMARY OF THE INVENTION

The present invention relates to a composition for regulating hair growth comprising a safe and effective amount of a supernatant derived from a culture of epithelial cells, preferably proliferating epithelial cells, which comprises a growth stimulating factor with characteristics of mitogenicity to dermal papilla cells, mitogenicity to 3T3 cells, lack of mitogenicity to epidermal cells, and a molecular weight of greater than about 3,000 daltons; and a pharmaceutically-acceptable carrier.

DETAILED DESCRIPTION OF THE INVENTION

As used herein, "mitogenicity" means an ability to stimulate growth (mitosis) in cells.

As used herein, "regulating hair growth" means inducing the formation of a greater number of hair strands, and/or increasing the diameter of the hair strand, and/or lengthening the hair strand, and/or preventing, retarding, or arresting the process of hair loss.

As used herein, "proliferating cells" means cells undergoing mitosis.

As used herein, "epithelial cells" refers to the cells which cover all the free sufaces, cutaneous, mucous, and serous, including the glands and other structures derived therefrom, e.g., corneal, esophegeal, epidermal, and hair follicle epithelial cells, but not including amnion epithelial cells. Such cells may be normal non-malignant cells, or transformed/immortalized cells.

As used herein, "hair follicle epithelial cells" refers to epithelial cells which surround the dermal papilla in the hair follicle, e.g., stem cells, outer root sheath cells, matrix cells, and inner root sheath cells. Such cells may be normal non-malignant cells, or transformed/immortalized cells.

As used herein, "epidermal cells" refers to epithelial cells in the epidermis. Such cells may be normal non-malignant cells, or transformed/immortalized cells.

As used herein, "epidermis" refers to the continuous stratified keratinizing cell layer encompassing the entire organism and terminating at bodily orifices in mucocutaneous junctions, but not including the hair follicle epithelial cells.

As used herein, "topical application" means directly laying on or spreading on outer skin.

As used herein, "transformed cells" refers to cells which have spontaneously converted to a state of unrestrained growth, i.e., they have acquired the ability to grow through an indefinite number of divisions in culture.

As used herein, "immortalized cells" refers to cells which have been altered via chemical and/or recombinant means such that the cells have the ability to grow through an indefinite number of divisions in culture.

As used herein, "cutaneous injection" means introduction of a substance immediately beneath or within the skin by a hypodermic needle.

As used herein, all percentages are by weight unless otherwise specified.

The compositions of the present invention comprise an epithelial cell derived growth factor which stimulates dermal papilla cell mitogenic activity and hence hair growth. In addition to its mitogenicity of dermal papilla cells, other characteristics of the growth factor include 1) mitogenicity to 3T3 cells, 2) a lack of mitogenicity to epidermal cells, 3) a molecular weight of greater than about 3,000 daltons, 4) sensitivity to chymotrypsin, and 5) retains 90% to 40% mitogenicity to dermal papilla cells following exposure to temperatures of 50° C. and 100° C. respectively for one hour.

The cell derived hair growth factor for use in the present invention may be obtained by culturing epithelial cells in nutrient medium followed by separation of the supernatant from such cultures, centrifuging the supernatant to remove cells and cell debris, and concentrating and dialysing the supernatant to isolate substances having an apparent molecular weight of about 3,000D.

The cell free concentrate so obtained contains the epithelial cell derived hair growth factor having an apparent molecular weight of about 3,000D. This hair growth factor is then incorporated in the compositions according to the invention together with a suitable vehicle. Alternatively, the cell free concentrate, following dialysis, can be dried, preferably by freeze drying, prior to incorporation in the compositions according to the invention.

Although the hair growth factor has an apparent molecular weight of about 3,000D, it is believed that certain fragments derived from the hair growth factor can also show activity in regulating hair growth.

According to a preferred embodiment of the invention, the cell free epithelial cell culture supernatant is concentrated at least 40 to 50 times, preferably at least 100 times, to provide a concentrate containing the hair growth factor, having a protein level not greater than 10 mg/ml, preferably 2 to 3 mg/ml.

The amount of the hair growth factor to be incorporated with a suitable vehicle into compositions for topical use can vary widely, but in general, an amount expressed as protein of from about 0.00001% to about 20%, preferably from about 0.001% to about 10%, more preferably from about 0.01% to about 5% by weight of the composition will provide an adequate dose of hair growth factor to the skin following topical application.

The amount of the hair growth factor to be incorporated with a suitable vehicle into compositions for cutaneous injection can vary widely, but in general, an amount expressed as a protein of from about 0.00001% to about 10%, preferably from about 0.001% to about 10%, more preferably from about 0.01% to about 10%, by weight of the composition will provide an adequate dose of hair growth factor to the target area following cutaneous injection.

The following examples are intended to illustrate the process for obtaining the growth stimulating factor as applied to a particular sample. It is not intended to limit the invention.

EXAMPLE I

Preparation of Epidermal Cell Derived Growth Stimulating Factor

Human foreskin epidermal cells are prepared according to the method of S. T. Boyce and R. G. Ham (J Tissue Culture Meth 9, 83–93, 1985) with the following modifications. After treatment of foreskin with collagenase, the epidermis is placed in 0.0125% trypsin in Hepes buffered saline. The epidermis is then triturated to release individual epidermal cells. The epidermal cells are grown in a cell culture medium of KGM (Clonetics; #3001). Epidermal cells are subcultured using 3.0 Units/ml dispase at 37° C. until the cells detach from the surface. KGM is then added at a volume ratio of 5:1 to dispase. The cell suspension is then transferred into a conical tube and centrifuged at 200×G for 5 min. The cells are resuspended with fresh KGM for plating. The cells are grown to passage #2 at which time they are rinsed and the culture medium changed to 'Keratinocyte Basal Medium' (medium which does not contain pituitary extract nor the following growth factors normally present in the culture medium, including, hydrocotisone, insulin, and epidermal growth factor; KBM Clonetics #3101). The epidermal cells are incubated in this medium for up to 48 hours at which time the culture medium is decanted. This medium ('Conditioned Defined Medium') is then centrifuged at 100,000×G for 30 minutes. The medium is fractionated and concentrated by ultrafiltration using an Amicon Centricon-3 filter having a molecular weight cutoff of about 3,000D. The retentate, having a molecular weight greater than about 3,000D, will contain all the growth factor activity as determined in the dermal papilla cell mitogen assay below, whereas there will be no activity in the filtrate which contains material having a molecular weight less than about 3,000D.

Alternative methods for fractionating and concentrating the conditioned medium can include dialyzing the medium against a membrane having a specific molecular weight cutoff, followed by lyophilizing the medium, and finally reconstituting the medium into a suitable buffer.

EXAMPLE II

Preparation of Human Follicle Epithelial Cell Derived Growth Stimulating Factor

Hair follicles are obtained from scalp biopsies. The follicles are carefully dissected out and immersed in Dulbecco's modified Eagle's Medium (DMEM) buffered with 25 mM HEPES (N-2-hydroxyethylpiperazine-N'-2-ethanesulfonic acid) and supplemented with antibiotics as described by H-J Stark et al (Differentiation 35, 236–248, 1987). The follicles are transferred into a 35 mm tissue culture dish containing the above medium. The medium is then aspirated and follicles covered with 0.1% trypsin (1:250) and 0.02% EDTA in phosphate-buffered saline (PBS) without calcium or magnesium and incubated for 10 minutes at 37° C. A single cell suspension is obtained by vigorously pipetting the follicles in DMEM supplemented with 10% newborn calf serum. If necessary, the follicles are sequentially treated with trypsin again. The cell suspension is collected and centrifuged at 200×G for 10 minutes. The cells are rinsed once again in DMEM without serum. The epithelial cells are grown in a cell culture medium of KGM (Clonetics; #3001). Epithelial cells are subcultured using 3.0 Units/ml dispase at 37° C. until the cells detach from the surface. KGM is then added at a volume ratio of 5:1 to dispase. The cell suspension is then transferred into a conical tube and centrifuged at 200×G for 5 min. The cells are resuspended with fresh KGM for plating. The cells are grown to passage #2 at which time cells are rinsed and the culture medium changed to 'Defined Medium' (medium which does not contain pituitary extract nor the following growth factors normally present in the culture medium, including hydrocotisone, insulin, and epidermal growth factor; KBM Clonetics #3101). The epithelial cells are incubated in this medium for up to 48 hours at which time the culture medium is decanted. This medium ('Conditioned Defined Medium') is then centrifuged at 100000×G for one hour. The medium is fractionated and concentrated by ultrafiltration using an Amicon Centricon-3 filter having a molecular weight cutoff of 3000D. The retentate having a molecular weight greater than 3000 will contain all the growth factor activity as determined in the dermal papilla cell mitogen assay below, whereas there will be no activity in the filtrate which contains material having a molecular weight less than 3000D.

Alternative methods for fractionating and concentrating the conditioned medium can include dialyzing the medium against a membrane having a specific molecular weight cutoff, followed by lyophilizing the medium, and finally reconstituting the medium into a suitable buffer.

EXAMPLE III

Dermal Papilla Cell Mitogen Assay

A. Preparation of Human Scalp Dermal Papilla Cells

The human scalp dermal papilla (hDP) cells are prepared using a modified procedure of existing methodologies (A. G. Messenger, Br J Dermatol 110, 685–689, 1984; and C. A. B. Jahoda and R. F. Oliver, Br J Dermatol 105, 623–627, 1981; and C. A. B. Jahoda and R. F. Oliver, J Embryol Exp Morph 79, 211–224, 1984). Human scalp skin is obtained from scalp reduction surgery and placed in ice-cold sterile Dulbecco's Modified Eagle's Medium/F-12 (1:1) containing 20% fetal calf serum and antibiotics. Within 48 hours of surgery, the skin is dissected, fat removed, and individual hair follicles collected and placed in ice-cold Chang medium (Hana Biological #T101-058) containing 10% Hyclone defined calf serum (Hyclone Lab #A-2151-L); ('Complete Chang'). The bulbs are cut off and microdissected to obtain the dermal papilla. Ten dermal papilla are collected in this fashion, transferred into a sterile conical tube containing 2 ml of Complete Chang medium, and centrifuged at 200×G for 5 min. The medium is aspirated and the dermal papilla are resuspended in 2 ml of Complete Chang containing Collagenase Type IV at 65 Units/ml. The collagenase is prepared as a 1 mg/ml stock in phosphate buffered saline. After 30 min at 37° C. in a shaking water bath, the dermal papilla are collected by centrifugation at 200×G for 5 min. The papilla pellet is rinsed once in Complete Chang and is transferred into a single well (2.0 cm$^2$) of a 24-well dish (Linbro #76-033-05) containing 0.5 ml of Complete Chang and incubated at 37° C. in a humidified atmosphere containing 5% $CO_2$.

Once the cells are observed to be growing out of the explant (generally three days), the culture medium is replaced three times weekly. As the cells become confluent, the cells are removed with 0.25% trypsin in Dulbecco's Balanced Salt Solution and are transferred into a 25 cm$^2$ T-25 cell culture flask (Passage #1) containing 5 ml of Complete Chang. Passage #3 hDP cells are used in the growth promoter assays. Each passage represents an approximate three-fold increase in dermal papilla cell number.

B. Dermal Papilla Cell Mitogen Assay

The following method is a measure of dermal papilla cell mitotic activity and can be used to detect growth factors (M. B. Spor and A. B. Roberts, Nature 332, 217–219, 1988). Human dermal papilla cells are plated to 20–40% confluency in 1:1 mixture of Complete Chang and Dulbecco's Modified Eagle's Medium ('DMEM' containing high glucose) containing 15% fetal calf serum and antibiotics ('Complete DMEM'). The following day the medium is changed to Complete DMEM. The following day the medium is changed to DMEM containing 0.5% fetal calf serum. During the last four hours of a 24 hour incubation, the cells are incubated with [methyl-$^3$-H]-thymidine. This time point represents the baseline mitotic activity of the dermal papilla cells. The radiolabelled cells are then solubilized in a solution containing 0.1% sodium dodecyl sulfate, 0.05 mM EDTA, and 1.0 mM Tris pH 8.0. Trichloroacetic acid and ethanol precipitable radiolabelled DNA is determined and normalized to the total content of cellular DNA in the sample (C. Lebarca and K. Paigen, Analyt Biochem 102, 344–351, 1980).

The remaining dermal papilla cells are then exposed to (a) fresh Complete DMEM (positive control) (b) fresh DMEM containing 0.5% fetal calf serum (negative control), (c) 1:1 mixture of fresh DMEM containing 0.5% fetal calf serum and Conditioned Defined Medium, or (d) 1:1 mixture of fresh DMEM containing 0.5% fetal calf serum and Conditioned Sham Medium. The media used in (c) and (d) is adjusted to a final fetal calf serum concentration of 0.5% and 1.0 mM $CaCl_2$ before adding to the hDP cells. During the last four hours of a 24 hour incubation, the cells are incubated with [methyl-$^3$-H]-thymidine. The cells are processed for acid and ethanol precipitable radiolabelled DNA as described above for the baseline measurement.

The results show that the Conditioned Defined Medium induces a significant increase in thymidine incorporation relative to the sham control.

EXAMPLE IV

3T3 Cell Mitogen Assay

The 3T3 cell mitogen assay is based on the assay described by Scher, C. D., et al. Nature 281, 390–392, 1979; Cohen, S. and Carpenter, G. Proc Nat Acad Sci, USA 72, 1317–1320, 1975; and Gospodarowicz, D. F. Biol Chem 2515–2520, 1975.

Balb/c 3T3 cells are plated and grown in a 24-well tissue culture dish in Dulbecco's Modified Eagle's Medium (DMEM) +10% newborn calf serum. The medium is changed three times a week until confluency, at which time the medium is changed to DMEM+0.5% serum. After changing the medium once during the next 48 hours the wells are split into groups of triplicate wells. In Group I, [$^3$H]-thymidine is added during the last 4 hours of the 48 hour period and subsequently processed for thymidine incorporation into cellular DNA ('Time Zero Baseline Control'). In Group II, the medium is changed to DMEM+0.5% serum and the cells incubated for an additional 24 hours, radiolabelled and processed as described ('Negative Control'). In Group III, the medium is changed to DMEM+10% serum and the cells incubated for an additional 24 hours, radiolabelled and processed as described ('Positive Serum Control'). In Group IV, the medium is changed to a 1:1 mixture of DMEM+0.5% serum and Conditioned Defined Medium. Prior to mixing the two media, the conditioned medium is adjusted to 0.5% serum and 1 mM $CaCl_2$. At the end of the 24 hour incubation, the cells are radiolabelled and processed as described. In Group V, the medium is changed to a 1:1 mixture of DMEM+0.5% serum and sham medium. Prior to mixing the two media, the sham is adjusted to 0.5% serum and 1 mM $CaCl_2$. At the end of the 24 hour incubation, the cells are radiolabelled and processed as described.

The resulting data will show that the Conditioned Defined Medium induces a significant increase in thymidine incorporation relative to the sham control.

EXAMPLE V

Epithelial Cell Mitogen Assay

Human foreskin epithelial cells and conditioned medium are prepared as previously described. For the mitogen assay, epithelial cells in passage #1 are dissociated with dispase and plated at 10-25% confluency in each well of a 8 well dish (8 $cm^2$) in complete KGM medium. The medium is changed 3 times per week until approximately 70% confluency is achieved. The cells remain in this medium for an additional 5 days to reduce mitogenic acitivity and deplete the medium of its growth factor activity. During the last four hours of this incubation, [methyl-$^3$H]-thymidine is added to one set of three wells ('baseline mitotic activity'). At the end of the four hour incubation period, the cells are rinsed and solubilized in a solution containing 0.1% sodium dodecyl sulfate, 0.05 mM EDTA, and 1.0 mM Tris pH 8.0. Trichloroacetic acid and ethanol/ether precipitable radiolabelled DNA is determined and normalized to the total content of cellular DNA in the sample. For the remaining cells, after the five day incubation, the medium ('old medium') is removed and saved. To one set of three wells old medium is added back ('negative control'). To a second set of wells, fresh KGM is added ('positive control'). To a third set of wells, a 1:1 mixture of old medium and conditioned defined medium is added ('test'). To a fourth set of wells a 1:1 mixture of old medium and sham conditioned medium is added ('sham control'). During the last four hours of a 24 hour incubation, the cells are incubated and radiolabelled with thymidine as described above.

The resulting data will show that Conditioned Defined Medium does not contain factors which are mitogenic to human epithelial cells relative to the sham control.

EXAMPLE VI

Sensitivity to Proteases

A. Protease Sensitivity: Trypsin

Conditioned medium derived from foreskin epidermal cells is prepared as described previously. The medium is treated with trypsin type III (Sigma T-8253) at a final concentration of up to 100 ug/ml at 37° C. for up to four hours. Soybean trypsin inhibitor type I-S (Sigma Y-9003) is then added to a final concentration of 1 mg/ml. The mixture is then centrifuged at 20000 G for thirty minutes, decanted, and filter sterilized. This medium is tested in the dermal papilla cell mitogen assay. The data show that the mitogenic activity of the conditioned medium is not affected by trypsin treatment relative to a control that is treated identically except without trypsin.

B. Protease Sensitivity: Chymotrypsin

Conditioned medium derived from foreskin epidermal cells is prepared as described previously. The medium is treated with chymotrypsin type I-S (Sigma C-7762) at a final concentration of up to 100 ug/ml at 37° C. for up to five hours. Soybean trypsin inhibitor type I-S (Sigma Y-9003) is then added to a final concentration of 1 mg/ml. The mixture is then centrifuged at 20000 G for thirty minutes, decanted, and filter sterilized. This medium is tested in the dermal papilla cell mitogen assay. The data show that the mitogenic activity of the conditioned medium significantly decreased relative to a control that is treated identically except without chymotrypsin.

EXAMPLE VII

Heat Sensitivity

Conditioned medium derived from foreskin epidermal cells is prepared as described previously. The medium is split into aliquots and heated in a waterbath at 50° C., 60° C., 70° C., 80° C., or 100° C. for thirty minutes. Medium is also kept in an icebath for thirty minutes. After this time period, the medium is centrifuged at 20000 G for thirty minutes, decanted, and filter sterilized. This medium is tested in the dermal papilla cell mitogen assay. The results show that there is a linear decline of growth factor activity from about 90% to about 40% after the conditioned medium is heated between about 50° C. and about 80° C. The growth factor activity remains at about 40% between about 80° C. and about 100° C.

Hair Growth Regulating Compositions

The present invention relates to compositions for regulating hair growth comprising a safe and effective amount of an epithelial cell derived hair growth factor having the characteristics of mitogenicity to dermal papilla cells, mitogenicity to 3T3 cells, a lack of mitogenicity to epidermal cells, and a molecular weight of greater than about 3,000 daltons; and a pharmaceutically acceptable carrier. As used herein, "safe and effective amount" means an amount of compound or composition sufficient to significantly induce a positive modification in the condition to be treated, but low enough to avoid serious side effects (at a reasonable benefit/risk ratio), within the scope of sound judgment.

The Carrier

The compositions of the present invention comprise a solid, semi-solid or liquid pharmaceutically acceptable carrier to enable the growth stimulating factors to be delivered to the desired target at an appropriate concentration. As used herein, "pharmaceutically acceptable carrier" means a filler/diluent substance which is suitable for administration to a human or lower animal. The carrier can itself be inert or it can possess physiological or pharmaceutical benefits of its own. The nature of the carrier will be dictated by the method chosen for administration of the composition. The method of administration of the growth stimulating factor composition may range from internal methods such as injection to external topical methods.

A preferred method of administration of the growth stimulating factors is by cutaneous injection. The carrier for facilitation of such administration would preferably comprise water or a saline solution.

A more preferred method of administration of the growth stimulating factors is by topical application. Topical application is preferably achieved with compositions in the forms of sprays, tonics, creams, lotions, shampoos, and the like.

Topical compositions of the present invention can be formulated as liquids, for example as a lotion, cream, shampoo, conditioner or milk. Such liquid compositions may be formulated for use in conjunction with an applicator such as a roll-ball applicator, or a spray device such as an aerosol can containing propellant, or a container fitted with a pump to dispense the liquid product.

Alternatively, the compositions of the invention can be solid or semi-solid, for example sticks, creams or gels. Such solid or semi-solid compositions may be formulated for use in conjunction with a suitable applicator or simply a tube, or bottle, or as a liquid-impregnated fabric, such as a tissue wipe.

The selection of a carrier for this purpose presents a wide range of possibilities depending on the required product form of the composition. Suitable vehicles can be classified as described hereinafter.

The term "topical carrier" refers to substances which can act as diluents, dispersants, or solvents for the growth stimulating factors which therefore ensure that it can be applied to and distributed evenly over the selected target at an appropriate concentration. The carrier is preferably one which can aid penetration of the growth stimulating factors into the skin to reach the immediate environment of the hair follicle. Topical carriers useful in compositions of the subject invention can include water as a vehicle, and/or at least one cosmetically acceptable vehicle other than water. Carriers useful in topical compositions according to the invention may include liposomes, latex latices, microphages, and various forms of microencapsulation of the growth stimulating factors.

Generally, the carrier is either organic in nature or an aqueous emulsion and capable of having the growth stimulating factors dispersed or dissolved therein. The carrier may include pharmaceutically-acceptable emollients, skin penetration enhancers, coloring agents, fragrances, emulsifiers, thickening agents, and solvents.

A more detailed description of preferred topical compositions follows:

1. Lotions

The lotions can comprise an effective amount (preferably from about 0.01% to about 10%, more preferably from about 0.1% to about 1%) of the growth stimulating factors; from 1% to 50%, preferably from 3% to 15%, of an emollient; the balance being water, a $C_2$ or $C_3$ alcohol, or a mixture of water and the alcohol. Several emollients are known. Examples of such emollients are as follows:

a. Hydrocarbon oils and waxes. Examples are mineral oil, petrolatum, paraffin, ceresin, ozokerite, microcrystalline wax, polyethylene, and perhydrosqualene.

b. Silicone oils, such as dimethylpolysiloxanes, methylphenylpolysiloxanes, water-soluble and alcohol-soluble siliconeglycol copolymers and volitile silicone fluids such as cyclomethicane.

c. Triglyceride fats and oils such as those derived from vegetable, animal and marine sources. Examples include castor oil, safflower oil, cotton seed oil, corn oil, olive oil, cod liver oil, almond oil, avocado oil, palm oil, sesame oil, and soybean oil.

d. Acetoglyceride esters, such as acetylated monoglycerides.

e. Ethoxylated glycerides, such as ethoxylated glyceryl monostearate.

f. Alkyl esters of fatty acids having 10 to 20 carbon atoms. Methyl, isopropyl and butyl esters of fatty acids are useful herein. Examples include hexyl laurate, isohexyl laurate, isohexyl palmitate, isopropyl palmitate, isopropyl myristate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.

g. Alkenyl esters of fatty acids having 10 to 20 carbon atoms. Examples thereof include oleyl myristate, oleyl stearate, and oleyl oleate.

h. Fatty acids having 8 to 22 carbon atoms. Suitable examples include pelargonic, lauric, myristic, palmitic, stearic, isostearic, hydroxystearic, oleic, linoleic, ricinoleic, arachidonic, behenic, and erucic acids.

i. Fatty alcohols having 8 to 22 carbon atoms. Lauryl, myristyl, cetyl, hexadecyl, stearyl, isostearyl, hydroxystearyl, oleyl, ricinoleyl, behenyl, erucyl, and 2-octyl dodecyl alcohols are examples of satisfactory fatty alcohols.

j. Fatty alcohol ethers. Ethoxylated fatty alcohols of 8 to 20 carbon atoms include the lauryl, cetyl, stearyl, isostearyl, oleyl, and cholesterol alcohols having attached thereto from 1 to 50 ethylene oxide groups or 1 to 50 propylene oxide groups, or a mixture thereof.

k. Ether-esters such as fatty acid esters of ethoxylated fatty alcohols.

l. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases ar illustrative of emollients derived from lanolin.

m. Polyhydric alcohols and polyether derivatives. Propylene glycol, dipropylene glycol, polypropylene glycol (M.W. 2000–4000), polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol (M.W. 200–6000), methoxy polyethylene glycols 350, 550, 750, 2000, 5000, poly[ethylene oxide] homopolymers (M.W. 100,000–5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol) $C_{15}$–$C_{18}$ vicinal glycol, and polyoxypropylene derivates of trimethylolpropane are examples thereof.

n. Polyhydric alcohol esters. Ethylene glycol mono- and di-fatty acid esters, diethylene glycol mono- and di-fatty acid esters, polyethylene glycol (M.W. 200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

o. Wax esters such as beeswax, spermaceti, myristyl myristate, stearyl stearate.

p. Beeswax derivatives, e.g., polyoxyethylene sorbitol beeswax. These are reaction products of beeswax with ethoxylated sorbitol of varying ethylene oxide content, forming a mixture of ether-esters.

q. Vegetable waxes including carnauba and candelilla waxes.

r. Phospholipids such as lecithin and derivatives.

s. Sterols. Cholesterol, cholesterol fatty acid esters are examples thereof.

t. Amides such as fatty acid amides, ethoxylated fatty acid amides, solid fatty acid alkanolamides.

The lotions further preferably comprise from 1% to 10%, more preferably from 2% to 5%, of an emulsifier. The emulsifiers can be nonionic, anionic or cationic. Examples of satisfactory nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene oxide, mono- and di-fatty acid esters of ethylene glycol wherein the fatty acid moiety contains from 10 to 20 carbon atoms, diethylene glycol, polyethylene glycols of molecular weight 200 to 6000, propylene glycols of molecular weight 200 to 3000, glycerol, sorbitol, sorbitan, polyoxyethylene sorbitol, polyoxyethylene sorbitan and hydrophilic wax esters. Suitable anionic emulsifiers include the fatty acid soaps, e.g. sodium, potassium and triethanolamine soaps, wherein the fatty acid moiety contains from 10 to 20 carbon atoms. Other suitable anionic emulsifiers include the alkali metal, ammonium or substituted ammonium alkyl sulfates, alkyl arylsulfonates, an alkyl ethoxy ether sulfonates having 10 to 30 carbon atoms in the alkyl moiety. The alkyl ethoxy ether sulfonates contain from 1 to 50 ethylene oxide units. Satisfactory cationic emulsifiers are the quaternary ammonium, morpholinium and pyridinium compounds. Certain of the emollients described in preceding paragraphs also have emulsifying properties. When a lotion is formulated containing such an emollient, an additional emulsifier is not needed, though it can be included in the composition.

The balance of the lotion is water or a $C_2$ or $C_3$ alcohol, or a mixture of water and the alcohol. The lotions are formulated by simply admixing all of the components together. Preferably the compound of the present invention is dissolved in the mixture. Conventional optional components can be included. One such additive is a thickening agent at a level from 1% to 10% of the composition. Examples of suitable thickening agents include: cross-linked carboxypolymethylene polymers, ethyl cellulose, polyethylene glycols, gum tragacanth, gum kharaya, xanthan gums and bentonite, hydroxyethyl cellulose, and hydroxypropyl cellulose.

2. Creams

The creams comprise an effective amount (preferably from about 0.01% to about 10%, more preferably from about 1% to about 5%) of the growth stimulating factors; from 5% to 50%, preferably from 10% to 25%, of an emollient; the balance being water. The emollients above described can also be used in the cream compositions. Optionally the cream form contains a suitable emulsifier, as previously described. When an emulsifier is included, it is in the composition at a level from 3% to 50%, preferably from 5% to 20%.

3. Solutions

The solution form comprises an effective amount (preferably from about 0.01% to about 10%, more preferably from about 0.1% to about 1%, of the growth stimulating factors; the balance being water and/or a suitable organic solvent. Suitable organic materials useful as the solvent or a part of a solvent system are as follows: propylene glycol, polyethylene glycol (M.W. 200–600), polypropylene glycol (M.W. 425–2025), glycerine, sorbitol esters, 1,2,6-hexanetriol, ethanol, isopropanol, diethyl tartrate, butanediol, and mixtures thereof. Such solvent systems can also contain water.

These compositions in solution form can be applied to the skin as is, or else can be formulated into an aerosol and applied to the skin as a spray-on. The aerosol compositions further comprise from 25% to 80%, preferably from 30% to 50%, of a suitable propellant. Examples of such propellants are the chlorinated, fluorinated and chlorofluorinated lower molecular weight hydrocarbons. Nitrous oxide, carbon dioxide, butane, and propane are also used as propellant gases. These propellants are used at a level sufficient to expel the contents of the container.

4. Gels

Gel compositions can be formulated by simply admixing a suitable thickening agent to the previously described solution compositions. Examples of suitable thickening agents have been previously described with respect to the lotions.

The gel compositions comprise an effective amount (preferably from about 0.01% to about 10%, more preferably from about 1% to about 5%) of the growth stimulating factors; from 5% to 75%, preferably from 10% to 50%, of an organic solvent as previously described; from 0.5% to 20%, preferably from 1% to 10% of the thickening agent; the balance being water.

5. Solids

Compositions of solid forms have use as stick-type compositions intended for application to the scalp or other parts of the body. Such compositions comprise an effective amount (preferably from about 0.01% to about 10%, more preferably from about 1% to about 5%) of the growth stimulating factors, and from 50% to 98%, preferably from 60% to 90%, of the previously described emollients. This composition can further comprise from 1% to 20%, preferably from 5% to 15%, of a suitable thickening agent, and optionally emulsifiers and water. Thickening agents previously described with respect to lotions are suitable herein.

Penetration Enhancers

The presence of a penetration enhancer can potentiate the benefit of the hair growth stimulating factor by improving its delivery through the stratum corneum to its site of action in the immediate environment of the hair follicle proximate to the dermal papilla.

The penetration enhancer can accordingly function in a variety of ways. It can, for example, improve the distribution of the hair growth promoter on the skin surface. Alternatively, it can increase its partition into the skin from the composition when applied topically, so aiding its passage to its site of action. Other mechanisms enhancing the benefit of the growth stimulating factors may also be involved.

Examples of penetration enhancers include, but are not limited to: 1-dodecylazacycloheptan-2-one in combination with certain $C_3-C_4$ diols or a 1-substituted azacycloalkyl-2-one (see U.S. Pat. No. 4,557,934, Cooper, issued Dec. 10, 1985); a binary combination of a $C_3-C_4$ diol and a "cell-envelope disordering compound" (see U.S. Pat. No. 4,552,872, Cooper, Loomans and Fawzi, issued Nov. 12, 1985); a binary combination of N-(2-hydroxyethyl) pyrolidone and a "cell-envelope disordering compound" (see U.S. Pat. No. 4,537,776, Cooper, issued Aug. 27, 1985); a compound comprising lauryl alcohol, diisopropyl sebacate, dibutyl sebacate, dioctyl adipate, propylene glycol dipelargonate, butyl laurate, ethyl myristate, butyl myristate, isopropyl palmitate, oleyl alcohol, diethyl sebacate, dioctyl sabacate, dioctyl azelate, hexyl laurate, ethyl caprate, butyl stearate, isopropyl isostearate, 2-ethylhexyl pelargonate, butyl benzoate, benzyl benzoate, benzyl salicylate, dibutyl phthalate and/or ethyl laurate (see U.S. Pat. No. 4,299,826, Luedders, issued Nov. 10, 1981); a sugar ester in combination with a sulfoxide or phosphine oxide (see U.S. Pat. No. 4,150,114, Smith, issued Apr. 17, 1979; U.S. Pat. No. 4,148,917, Smith, issued Apr. 10, 1979; U.S. Pat. No. 4,148,887, Smith, issued Apr. 10, 1979; U.S. Pat. No. 4,148,874, Smith, issued Apr. 10, 1979; U.S. Pat. No. 4,148,893, Smith, issued Apr. 10, 1979; U.S. Pat. No. 4,130,667, Smith, Dec. 19, 1978; U.S. Pat. No. 4,130,643, Smith, issued Dec. 19, 1978; U.S. Pat. No. 4,046,886, Smith, issued Sep. 6, 1977; U.S. Pat. No. 3,952,099, Smith, issued Apr. 20, 1976; U.S. Pat. No. 3,952,099, Smith, issued Apr. 20, 1976; U.S. Pat. No. 3,896,238, Smith, issued Jul. 22, 1975); a carrier comprising alaphatic sulfoxides (See U.S. Pat. No. 3,953,599, MacMillan and Lyness, issued Apr. 27, 1976; U.S. Pat. No. 3,903,256, MacMillan and Lyness, issued Sep. 2, 1975; U.S. Pat. No. 3,839,566, MacMillan and Lyness, issued Oct. 1, 1974; U.S. Pat. No. 3,678,156, MacMillan and Lyness, issued Jul. 18, 1972); a carrier comprising a binary combination of a $C_3-C_4$ diol or $C_3-C_6$ triol and a specific $C_{16}$ or $C_{18}$ alcohol polar lipid compound (See European Patent Application 249 397, Kasting, Smith, Massaro and Snyder, published Dec. 16, 1987); a carrier comprising a $C_3-C_4$ diol, diol ester or diol ether and a cell-envelope disordering compound (See European Patent Application 095 813, Cooper, published Dec. 7, 1983; European Patent Application 043 738, Wickett, Cooper and Loomans, published Jan. 13, 1982); a carrier comprising a $C_6-C_{14}$ primary alkanol and a propane or butane diol (See European Patent Application 013 459, Wickett, Cooper and Loomans, published Jul. 23, 1980);

Other Hair Growth Stimulants

The composition according to the invention can also optionally comprise other hair growth stimulants capable of functioning in different ways to enhance the benefit of the growth stimulating factors. Examples of other substances which themselves possess the ability to regulate hair growth include, but are not limited to, minoxidil, retinoic acid, diazoxide, gly-his-lys (also known as liver cell growth factor) and its transition metal derivatives, cyclosporine, anti-inflammatories, calcium channel blockers, anti-bacterials, nonionic surfactants, mucopolysaccharides, antiandrogens, glycosidase inhibitors, and glycosaminoglycanase inhibitors.

Protein Stabilizing Agents

The hair growth factor is proteinaceous, and therefore its benefit in promoting hair growth can be maintained or improved by including a protein stabilizing agent in the composition according to the invention. As an example of this effect, it is to be noted that the skin contains natural proteases which might at least partially degrade the hair growth promoter. Therefore, the presence of a protein stabilizing agent such as a protease inhibitor or a secondary protein which will compete with the hair growth promoter for degradation by the natural skin proteases, can protect the hair growth promoter until it reaches the immediate environment of the hair bulb.

Examples of a protein stabilizing agent accordingly include glycerol, ethylenediaminetetraacetic acid, cysteine, $a_2$-macroglobulin, serum, and other proteinase inhibitors.

Other Ingredients

The composition according to the invention can contain ingredients other than those already mentioned, depending on the form of the intended product. It is, for example, possible to include antiseptics, preservatives, antioxidants, coloring agents, soaps and detergents.

The composition according to the invention can also be employed as a vehicle for a wide variety of cosmetically or pharmaceutically active ingredients, particularly ingredients which have some beneficial effect when applied to the skin other than the promotion of hair growth.

The composition according to the invention can also optionally comprise a perfume in an amount sufficient to make the composition acceptable to the consumer and pleasant to use. Usually, the perfume will form from 0.01% to 0.1% by weight of the composition.

Use of Compositions to Induce, Maintain or Increase Hair Growth

The invention also provides for the use of the hair growth factors isolated from cultured epithelial cells in the treatment of baldness. The following methods of use may be used to reverse, arrest, or prevent the onset of baldness.

The compositions according to the invention are preferably intended for application by cutaneous injection. The amount of the composition and the frequency of cutaneous injection can vary widely, depending on personal needs. As an example of application by cutaneous injection, it is suggested that a composition suitable for cutaneous injection comprising the growth stimulating factors be cutaneously injected preferably from once per day to once every six months, more preferably from three times per week to once per month, and most preferably from once per week to twice per month. The composition for cutaneous injection will contain from about 4 pg/kg to about 4 µg/kg, of the growth stimulating factors per dose, preferably from about 400 pg/kg to about 4 µg/kg, more preferably from about 2 ng/kg to about 3 µg/kg, and most preferably from about 50 ng/kg to about 0.3 µg/kg. The period of injections would be over a period of from about one month to about ten years, preferably from about three months to about two years, more preferably from about six months to about one year, thereby resulting in regulation of hair growth.

A more preferred method of applying the compositions according to the present invention involves topical application to the scalp of a human subject to regulate hair growth, particularly where the head is already bald, or where there is evidence to suggest a person will go bald (i.e., hair loss). The amount of the composition and the frequency of application to the hair and/or scalp can vary widely, depending on personal needs, but it is suggested as an example that topical application range from about 1 to about 10 times daily, preferably from about 2 to about 6 times daily, more preferably from about 3 to about 4 times daily, and most preferably once per day. The composition for topical application will contain from about 1 ng/cm$^2$ to about 1 mg/cm$^2$ of the growth stimulating factor per dose, preferably from about 100 ng/cm$^2$ to about 0.9 mg/cm$^2$, more preferably from about 0.5 $\mu$g/cm$^2$ to about 0.7 mg/cm$^2$, and most preferably from about 10 $\mu$g/cm$^2$ to about 0.5 mg/cm$^2$. The period of topical application would preferably be over a period of from about one month to about ten years, more preferably from about three months to about two years, more preferably still from about six months to about one year, thereby resulting in regulation of hair growth.

The following examples further describe and demonstrate the preferred embodiments within the scope of the present invention. The examples are given solely for the purpose of illustration, and are not to be construed as limitations of the present invention since many variations thereof are possible without departing from its spirit and scope.

Examples VIII–X illustrate a tonic according to the invention which is suitable for topical application to the scalp in order to promote hair growth. The lotion has the following formulation:

|  | Example VIII (% w/w) | Example IX (% w/w) | Example X (% w/w) |
|---|---|---|---|
| Hair growth factor | 0.1 | 1.0 | 10.0 |
| Ethanol | 10.0 | 15.0 | 15.0 |
| Glycerol | 1.0 | 2.0 | 3.0 |
| Perfume | 0.2 | 0.2 | 0.2 |
| Water | qs | qs | qs |

The tonic is applied to the scalp at a dose of one ml, once per day. As the response becomes noticeable, one may reduce the frequency of application.

Examples XI–XIII illustrate a lotion which can be used topically in the treatment of bald or balding male and female heads.

|  | Example XI (% w/w) | Example XII (% w/w) | Example XIII (% w/w) |
|---|---|---|---|
| Hydroxyethyl cellulose | 0.4 | — | 0.4 |
| Absolute ethanol | 15.0 | 15.0 | 15.0 |
| Propane-1,2-diol | — | — | 30.6 |
| Butane-1,3-diol | 33.4 | 33.4 | — |
| Paramethyl benzoate | 0.2 | 0.2 | 0.2 |
| Hair growth factor | 1.0 | 0.1 | 5.0 |
| Perfume | 0.5 | 0.5 | 0.5 |
| Water | qs | qs | qs |

The lotion is applied to the scalp at a dose of one ml, once per day. As the response becomes noticeable, one may reduce the frequency of application.

Example XIV illustrates a water-in-oil emulsion containing a hair growth factor according to the invention.

|  | Example XIV (% w/w) |
|---|---|
| Oily Phase |  |
| Sorbitan monooleate | 20.0 |
| Quaternium-18 hectorite | 5.0 |
| Liquid paraffin | 75.0 |
| Aqueous Phase |  |
| Hair growth promoter | 1.0 |
| Xanthan gum | 1.0 |
| Preservative | 0.3 |
| Perfume | 0.2 |
| Sodium chloride (1% w/w solution) | qs |

The emulsion was prepared by taking 10 parts by volume of the oily phase and to it adding slowly with stirring 90 parts by volume of the aqueous phase.

Example XV illustrates an oil-in-water cream containing a hair growth factor according to the invention.

|  | Example XV (% w/w) |
|---|---|
| Oil Phase |  |
| Cetearyl alcohol | 5.0 |
| Silicone oil, 200 fluid | 1.0 |
| Isopropyl myristate | 2.0 |
| Sodium stearoyl-2-lactylate | 2.0 |
| Aqueous Phase |  |
| Propylene glycol | 5.0 |
| Sodium citrate | 0.2 |
| Hair growth factor | 0.1 |
| Perfume | 0.1 |
| Purified water | qs to 100 |

The cream was prepared by mixing the oil phase and heating to 65° C. Combine the aqueous phase and heat to 70° C. Add the aqueous phase to the oil phase with suitable agitation. Mix with moderate agitation while cooling.

The following examples XVI–XVIII illustrate shampoos for use in washing the hair and scalp, and for regulating hair growth on the scalp.

|  | Example XVI (% w/w) |
|---|---|
| Sodium lauryl ether sulphate (2 EO): 21% AD | 41.4 |
| Lauryl dimethylamino acetic acid betaine: 30% AD | 4 |
| Coconut fatty acid diethanolamine | 1.5 |
| Oleth-3-phosphate (CRODAFOS N 3 Acid ®; Croda) | 1 |
| PEG-15 Tallow Polyamine (POLYQUART H ®; Henkel): 50% active | 1.5 |
| Preservative, coloring matter, salt | 0.58 |
| Hair growth factor | 10.0 |
| Perfume | qs |
| Water | to 100 |

|  | Example XVII (% w/w) |
|---|---|
| Sodium lauryl ether sulphate (2 EO): 100% AD | 12 |
| POLYQUART H ®: 50% active | 2.5 |
| CRODAFOS N 3 Acid ® | 2.5 |

|  | Example XVII (% w/w) |
| --- | --- |
| Hair growth factor | 8.0 |
| Zinc Sulphate | 5 |
| Perfume | qs |
| Water | to 100 |

|  | Example XVIII (% w/w) |
| --- | --- |
| Monoethanolamine lauryl sulphate: 100% AD | 20 |
| POLYQUART H ®: 50% active | 3 |
| CRODAFOS N 3 Acid ® | 1.7 |
| Coconut diethanolamide | 5 |
| Hair growth factor | 10 |
| Perfume | qs |
| Water | to 100 |
| pH adjusted to 6.5 | |

The shampoo is applied to the scalp at a dose of one ml. The shampoo is rubbed onto the scalp, and then rinsed off. The shampoo is reapplied to the scalp, rubbed onto the scalp and rinsed off.

Examples XIX-XXVII illustrate lotions according to the invention, each containing an activity enhancer which can be used topically in the treatment of bald or balding male or female heads, in order to regulate hair growth.

|  | Example XIX (% w/w) | Example XX (% w/w) | Example XXI (% w/w) |
| --- | --- | --- | --- |
| Minoxidil | 0.5 | 2.0 | 5.0 |
| Absolute ethanol | 20.0 | 20.0 | 20.0 |
| Propylene glycol | 30.0 | 30.0 | 30.0 |
| Hair growth factor | 5.0 | 1.0 | 0.1 |
| Perfume | 0.2 | 0.2 | 0.2 |
| Water | qs | qs | qs |

|  | Example XXII (% w/w) | Example XXIII (% w/w) | Example XXIV (% w/w) |
| --- | --- | --- | --- |
| Cu II: Gly-nis-lys-n-octyl ester | 0.1 | 1.0 | 5.0 |
| Absolute ethanol | 20.0 | 20.0 | 20.0 |
| Propylene Glycol | 30.0 | 30.0 | 30.0 |
| Hair growth factor | 5.0 | 2.0 | 0.5 |
| Perfume | 0.2 | 0.2 | 0.2 |
| Water | qs | qs | qs |

|  | Example XXV (% w/w) | Example XXVI (% w/w) | Example XXVII (% w/w) |
| --- | --- | --- | --- |
| Furildioxime | 0.1 | 1.0 | 5.0 |
| Absolute ethanol | 20.0 | 20.0 | 20.0 |
| Propylene glycol | 30.0 | 30.0 | 30.0 |
| Hair growth factor | 10.0 | 3.0 | 1.0 |
| Perfume | 0.2 | 0.2 | 0.2 |
| Water | qs | qs | qs |

The following Examples XXVIII and XXIX illustrate injectable forms of the hair growth factor for promoting hair growth on the scalp.

|  | Example XXVIII (% w/w) | Example XXIX (% w/w) |
| --- | --- | --- |
| Hair growth promoter | 0.1 | 0.1 |
| Ringer's solution | qs | — |
| Lactated Ringer's solution | — | qs |

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

What is claimed is:

1. A composition for regulating hair growth comprising:
   a. a safe and effective amount of a supernatant derived from a culture of epithelial cells which comprises a growth stimulating factor, the factor having the following characteristics:
      i. mitogenicity to dermal papilla cells,
      ii. mitogenicity to 3T3 cells,
      iii. lack of mitogenicity to epidermal cells, and
      iv. a molecular weight of greater than about 3,000 daltons; and
   b. a pharmaceutically-acceptable carrier.

2. The composition of claim 1 wherein the growth stimulating factor has the additional characteristic of decreased dermal papilla cell mitogen assay activity following treatment with chymotrypsin type I-S at a final concentration of up to about 100 µg/ml at about 37° C. for about 5 hours.

3. The composition of any of claims 1 or 2 wherein the growth stimulating factor has the additional characteristic of retaining from about 40% to about 90% dermal papilla cell mitogen assay activity following heat treatment from about 50° to about 100° C.

4. The composition of claim 1 wherein the composition comprises from about 0.01% to about 10% of the growth stimulating factor and the carrier is a topical carrier.

5. The composition of claim 4 wherein the cells are hair follicle epithelial cells.

6. The composition of claim 4 wherein the cells are epidermal cells.

7. The composition of claim 1 wherein the carrier is an injectable carrier.

8. The composition of claim 4 wherein the topical carrier comprises from about 1% to about 50% of an emollient.

9. The composition of claim 1 which additionally comprises a safe and effective amount of minoxidil.

10. A method of regulating hair growth which comprises topically applying to mammalian skin or hair any of the compositions of claims 1, 4, 5, 6 or 8.

11. A method of regulating hair growth which comprises cutaneous injection of the composition of claim 1.

* * * * *

UNITED STATES PATENT AND TRADEMARK OFFICE
CERTIFICATE OF CORRECTION

PATENT NO. : 5,130,142
DATED : July 14, 1992
INVENTOR(S) : Teresa K. Wong & Raphael Warren It is certified that error appears in the above-identified patent and that said Letters Patent is hereby corrected as shown below:

Column 4, line 8, "Meth 9," should read --Meth 9,--.

Column 4, line 55, "35" should read --35--.

Column 5, line 37, "110" should read --110--.

Column 5, line 39, "105" should read --105--.

Column 5, line 40, "79" should read --79--.

Column 6, line 10, "332" should read --332--.

Column 6, line 28, "102" should read --102--.

Column 6, line 51, "281" should read --281--.

Column 6, line 53, "72" should read --72--.

Column 6, line 54, "Chem 2515-2520" should read --Chem 250, 2515-2520--.

Column 10, line 42, "ar" should read --are--.

Signed and Sealed this

Ninth Day of November, 1993

Attest:

BRUCE LEHMAN

*Attesting Officer*    *Commissioner of Patents and Trademarks*